(12) United States Patent
Juttu et al.

(10) Patent No.: US 7,906,696 B2
(45) Date of Patent: Mar. 15, 2011

(54) PROCESS OF USING ZEOLITE CATALYST FOR HYDROCARBON CONVERSION

(75) Inventors: Gopalakrishnan G. Juttu, Sugar Land, TX (US); Robert Scott Smith, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 993 days.

(21) Appl. No.: 11/656,182

(22) Filed: Jan. 22, 2007

(65) Prior Publication Data

US 2008/0177119 A1    Jul. 24, 2008

(51) Int. Cl.
*C07C 2/52*           (2006.01)
(52) U.S. Cl. ............................ 585/419; 585/418; 585/417
(58) Field of Classification Search ................... 585/417, 585/418, 419
See application file for complete search history.

(56) References Cited

U.S. PATENT DOCUMENTS

| | | |
|---|---|---|
| 3,702,886 A | 11/1972 | Argauer et al. |
| 4,766,265 A | 8/1988 | Desmond et al. |
| 4,835,336 A | 5/1989 | McCullen |
| 4,861,932 A | 8/1989 | Chen et al. |
| 4,891,463 A | 1/1990 | Chu |
| 5,672,796 A | 9/1997 | Froment et al. |
| 6,784,333 B2 | 8/2004 | Juttu et al. |
| 2004/0192539 A1 | 9/2004 | Juttu et al. |

OTHER PUBLICATIONS

"Cyclar: One Step Processing of LPG to Aromatics and Hydrogen'"; Anderson et al.; AIChE Spring National Meeting, Houston, Texas (Mar. 24-28, 1985).

*Primary Examiner* — Thuan Dinh Dang
(74) *Attorney, Agent, or Firm* — Jim D. Wheelington

(57) ABSTRACT

This invention is for a catalyst for conversion of a hydrocarbonaceous feed. The catalyst is a zeolite aluminosilicate with a silicon to aluminum molar ratio from about 70:1 to about 100:1 on which a noble metal has been deposited. The zeolite catalyst may contain other optional tetravalent and trivalent elements in the zeolite framework. The zeolite structure may be MFI, FAU, TON, MFL, VPI, MEL, AEL, AFI, MWW or MOR. The catalyst is synthesized by preparing a zeolite containing aluminum, silicon and, optionally, other elements, such as germanium, in the framework, depositing a noble metal, such as platinum, on the zeolite and calcining the zeolite. The catalyst may be used for aromatization of alkanes to aromatics. One embodiment is a MFI zeolite catalyst which may be used for the aromatization of alkanes having two to six carbon atoms per molecule to aromatics, such as benzene, toluene and xylenes.

24 Claims, 4 Drawing Sheets

PROCESS OF USING ZEOLITE CATALYST FOR HYDROCARBON CONVERSION

BACKGROUND OF THE INVENTION

1. Field of the Invention

This invention relates to a catalyst for conversion of a hydrocarbonaceous feed, for example, a zeolite catalyst for aromatization of alkanes to aromatics, e.g., a MFI-type zeolite catalyst for the aromatization of alkanes having two to six carbon atoms per molecule to aromatics, such as benzene, toluene and xylenes.

2. Description of the Prior Art

Zeolite is a crystalline hydrated aluminosilicate that may contain other metals in the framework of the zeolite crystal or deposited, exchanged or impregnated onto the zeolite. A method for preparing a zeolite comprises (a) preparing an aqueous mixture of silicon oxide and sources of oxides of aluminum; and (b) maintaining said aqueous mixture under crystallization conditions until crystals of zeolite form. Zeolite by itself is known as an operative catalyst for many hydrocarbon conversion reactions but selectivity to a particular product may be low. Much zeolite research has focused on the zeolite framework containing elements other than silicon and aluminum and on depositing particular metals on the surface of the zeolite.

U.S. Pat. No. 5,672,796 discloses a catalyst and process for aromatizing one or more C3 to C6 saturated hydrocarbon with a partially sulfided Pt/Re loaded crystalline aluminosilicate molecular sieve of MFI structure and a Si/Al ratio between about 40 to about 600 to produce benzene, toluene, xylenes and ethane or ethane and propane with low methane content.

U.S. Pat. No. 4,766,265 discloses a process for the conversion of ethane to liquid aromatic hydrocarbons with a gallium modified molecular sieve catalyst promoted with rhenium and one of nickel, palladium, platinum rhodium and iridium. The molar ratio of silicon to M where M is aluminum, boron or gallium is in the range of about 10:1 to about 100:1, preferably ranging from about 20:1 to about 50:1.

U.S. Pat. No. 4,835,336 discloses a process for converting a C6-C12 paraffinic hydrocarbon feed to aromatics with a noble metal/low acidity medium pore size zeolite catalyst which has been presulfided. Adding a sulfur compound such as H2S, SO2 or an organic sulfur compound to the feed is an alternative to presulfiding. The silica to alumina mole ratio was disclosed as at least 12, preferably at least about 30, and could be 1600 and above. The example was a ZSM-5 having a silica to alumina ratio of 26,000:1.

U.S. Pat. No. 4,861,932 discloses a process for converting a C2-C12 paraffinic hydrocarbon feed to aromatics by contacting the feed with a noble metal/low acidity medium pore size zeolite catalyst in a first conversion zone then passing the resulting hydrocarbon mixture through a second conversion zone and contacting it with a medium pore size acidic zeolite catalyst. The silica to alumina mole ratio was disclosed as at least 12, preferably at least about 30, and could be 1600 and above. The example was a Pt/ZSM-5 having a starting silica to alumina ratio of 26,000:1 in the first conversion zone and a Ga/Ti-ZSM-5 having a starting silica to alumina ratio of 70:1 in the second conversion zone.

U.S. Pat. No. 4,891,463 discloses a process for converting C2 to C12 aliphatic hydrocarbons to aromatics with a crystalline zeolite catalyst containing gallium. The final catalyst will usually have a silica/alumina ratio of at least about 12. Preferably the silica/alumina ratio is about 500 to 26,000. The catalyst may contain an added metal which is gallium or any of the various suitable metals in Groups I through VIII of the Periodic Table including zinc, platinum, rhenium, cobalt, titanium, tellurium, sodium, nickel, chromium, aluminum, copper, palladium, calcium and rare earth metals.

It would be advantageous to have a zeolite-type catalyst which maintained relatively constant selectivity for conversion of lower alkanes, such as alkanes having two to six carbon atoms per molecule, to aromatics, such as benzene, toluene and xylene, over a period of time on stream.

SUMMARY OF THE INVENTION

The catalyst is a zeolite aluminosilicate with a silicon to aluminum molar ratio of about 70:1 to about 100:1 on which a noble metal has been deposited. The catalyst is synthesized by preparing a zeolite containing aluminum, silicon and, optionally, another element, such as germanium, in the framework, depositing a noble metal, such as platinum, on the zeolite and calcining the zeolite. Examples of the zeolite structure are MFI, FAU, TON, MFL, VPI, MEL, AEL, AFI, MWW or MOR. A specific example of the zeolite structure is MFI or ZSM-5. One use for the catalyst is in a process for aromatization of alkanes by contacting the zeolite catalyst with at least one alkane at aromatization conditions and recovering the aromatic product.

BRIEF DESCRIPTION OF THE DRAWINGS

A more complete appreciation of the invention and many of the attendant advantages thereof will be readily understood by reference to the following detailed description when considered in connection with the accompanying drawings.

DETAILED DESCRIPTION OF THE INVENTION

Figure 1:
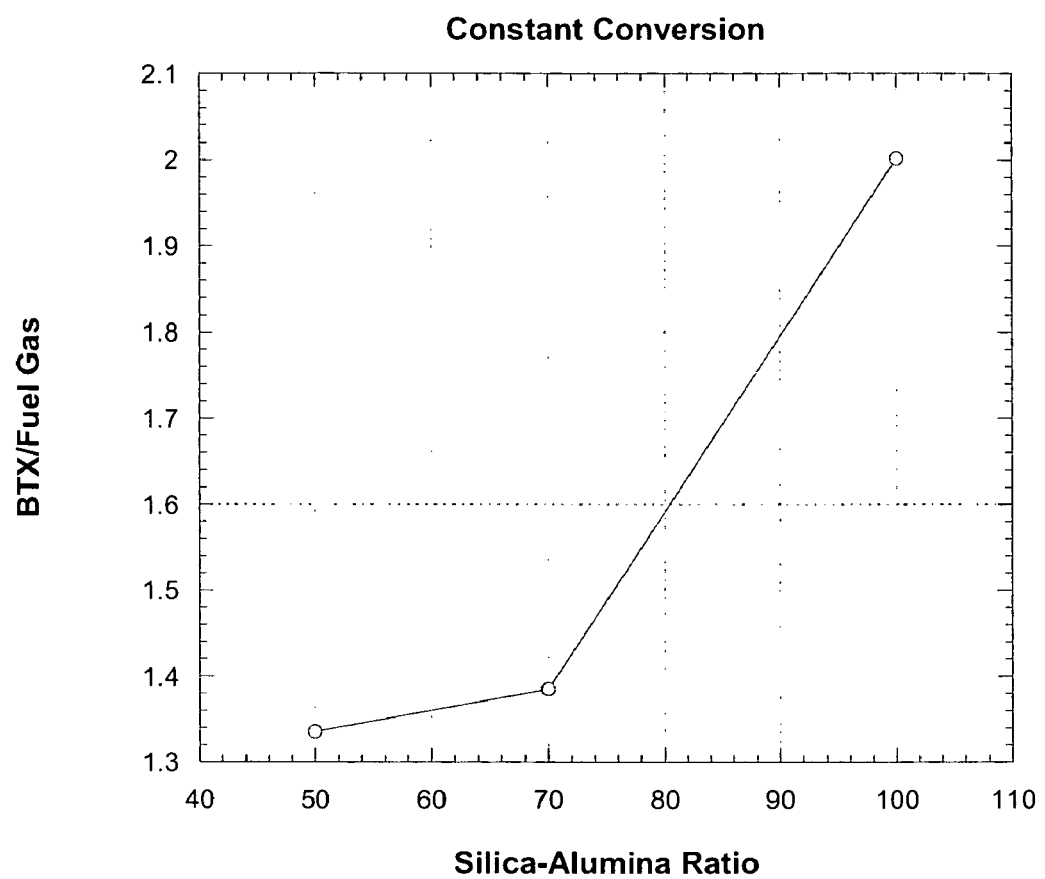
FIG. 1 shows silica to alumina molar ratio v. ratio of BTX/fuel gas product (g/g) at constant conversion of propane to BTX and fuel gas
Figure 2:
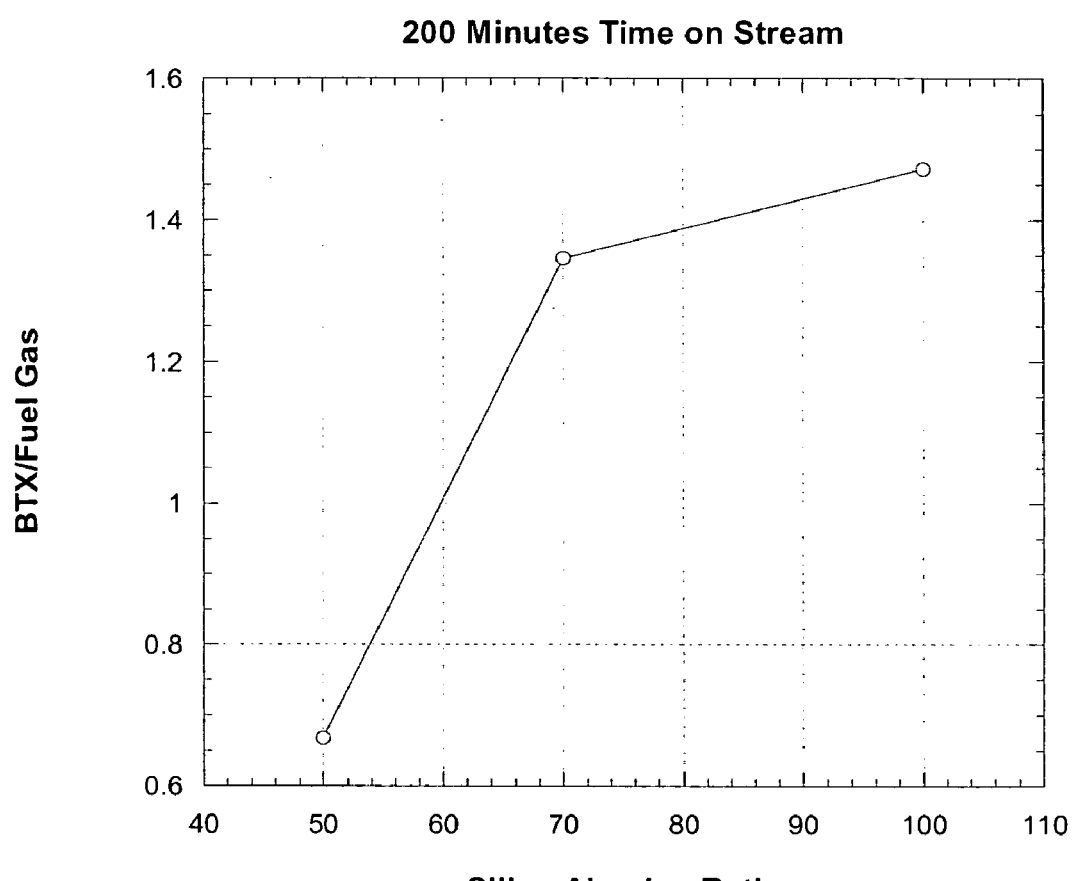
FIG. 2 shows silica to alumina molar ratio v. ratio of BTX/fuel gas product (g/g) at 200 minutes time on stream
Figure 3:
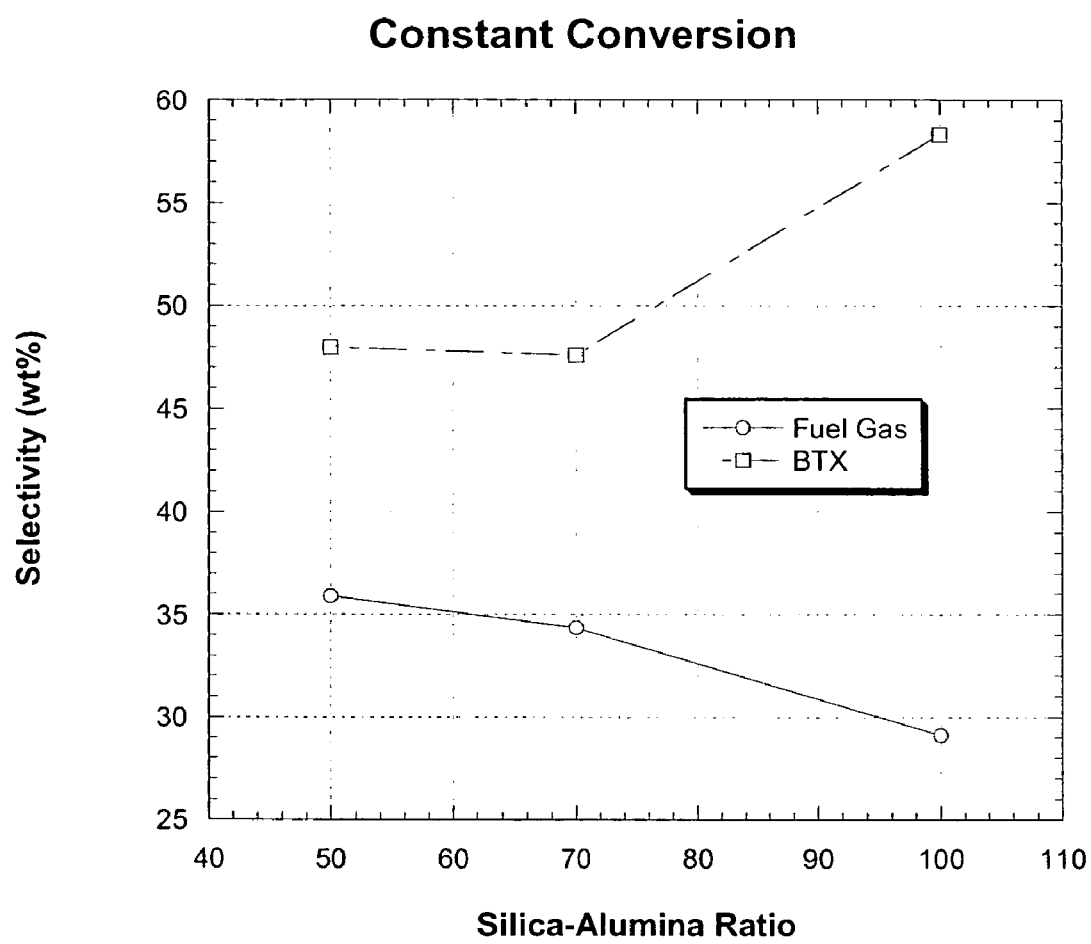
FIG. 3 shows silica to alumina molar ratio v. selectivity to BTX and to fuel gas at constant conversion
Figure 4:
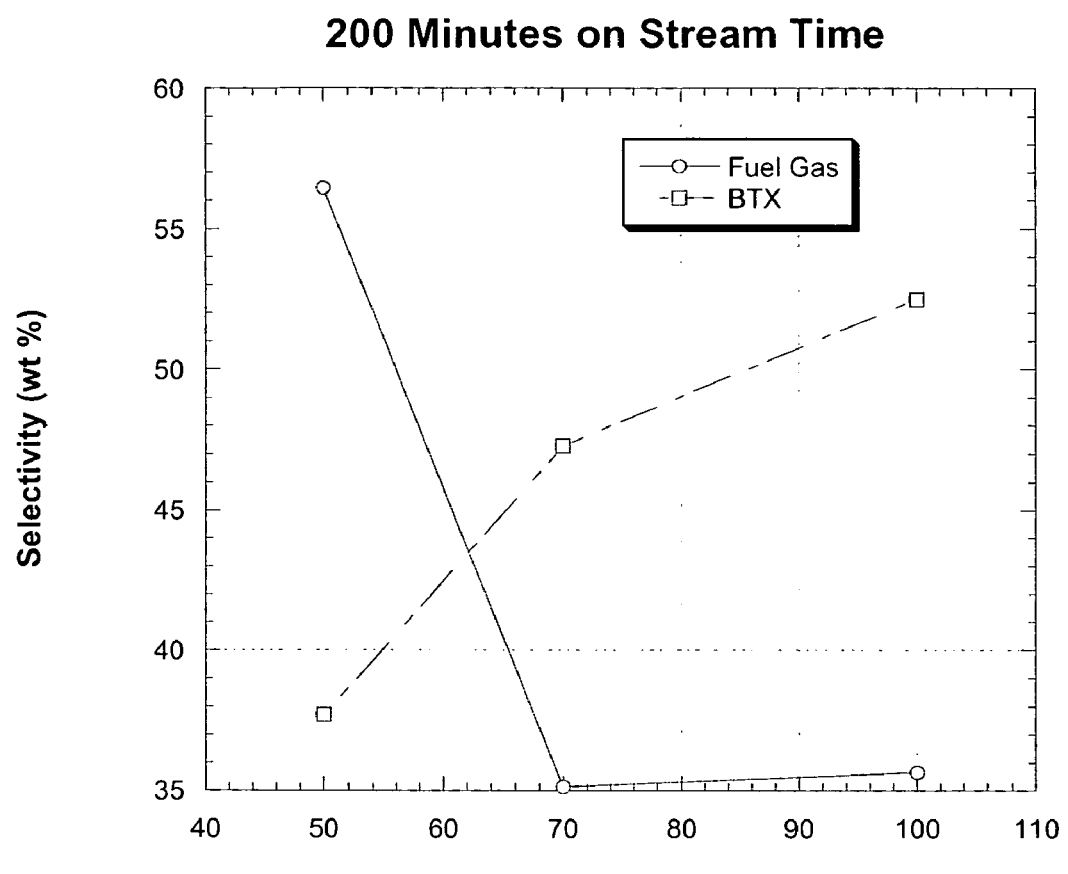
FIG. 4 shows silica to alumina molar ratio v. selectivity to BTX and to fuel gas at 200 minutes time on stream

Depositing platinum on a zeolite catalyst precursor in which germanium has been introduced into the aluminosilicate framework of the zeolite has been found to produce a catalyst that has increased stability with time on stream, i.e., maintains relatively constant selectivity for lower alkanes to aromatics, e.g., alkanes having two to six carbon atoms per molecule to benzene, toluene and xylenes. An example of such a catalyst, method of making a catalyst and method of using a catalyst is disclosed and claimed in U.S. Pat. No. 6,784,333, hereby incorporated by reference.

The zeolite of the present invention can be prepared by any known method of preparing an aluminosilicate structure of aluminum and silicon. Zeolites are known to be crystallized silicates and include structures of $TO_4$ tetrahedra, which form a three dimensional network by sharing oxygen atoms where T represents tetravalent silicon and trivalent aluminum. Tetravalent elements, such as germanium, tin, lead, zirconium, titanium, vanadium or chromium, may be substituted for the silicon. Trivalent elements such as gallium, boron, indium, thallium or iron, may be substituted for the aluminum. These tetravalent and trivalent elements would be in the framework of the zeolite crystal. Other elements which may be in the framework of the zeolite crystal are zinc or phosphorus.

Zeolites generally crystallize from an aqueous solution. The typical technique for synthesizing zeolites comprises converting an amorphous gel to zeolite crystals by a hydrothermal process, employing a dissolution/recrystallization mechanism. The reaction medium also contains structuring agents which are incorporated in the microporous space of the zeolite network during crystallization, thus controlling the construction of the network and assisting to stabilize the structure through the interactions with the zeolite components.

Methods of preparation of a MFI zeolite can also be found in U.S. Pat. No. 3,702,886 and in J. Phys. Chem, vol. 97, p. 5678-5684 (1993), hereby incorporated by reference.

The noble metal is deposited on the zeolite by any known method of depositing a metal on a zeolite. Typical methods of depositing a noble metal on zeolite are ion exchange and impregnation. The noble metal is present preferably in the range from 0.05% to 3% by weight, more preferably in the range from 0.2% to 2% by weight and most preferably in the range from 0.2 to 1.5% by weight. The present invention may contain any noble metals, examples of which are palladium, silver, platinum and gold.

The silica to alumina molar ratio ($SiO_2:Al_2O_3$) of the zeolite catalyst in the present invention is meant to represent the ratio in the framework of the zeolite crystal and to exclude silicon or aluminum from another source. The silica to alumina molar ratio may be estimated by calculation based on the silicon and aluminum components used in the synthesis of the zeolite and confirmed or determined by any known conventional method of analysis, such as inductively coupled plasma (ICP) or X-ray fluorescence (XRF). Although zeolites with silica to alumina mole ratios of at least 12:1 and zeolites with relatively high silica to alumina ratios of at least 500:1 or above up to essentially aluminum-free are operative in the aromatization of alkanes having two to six carbon atoms per molecule to aromatics, the silica to alumina molar ratio of the present invention is in the range from 70:1 to 100:1. Zeolite catalysts in this silica to alumina molar ratio range having a noble metal deposited on the zeolite have been found to have improved selectivity to aromatics, such as benzene, toluene and xylenes, rather than fuel gas. Fuel gas is the byproduct of an alkane aromatization reaction and is alkanes of much lower value than the product aromatics or the feedstream alkanes. Generally, the two principal components of fuel gas are methane and ethane.

The catalyst may be bound by oxides of magnesium, aluminum, titanium, zirconium, thorium, silicon, boron and mixtures thereof. Preferably, the support is an oxide of silicon (silica).

The catalyst preferably has average pore size preferably in the range from 5 angstroms to 100 angstroms, more preferably in the range from 5 angstroms to 50 angstroms and most preferably in the microporous range from 5 angstroms to 20 angstroms.

The catalyst may contain a reaction product, such as a sulfide of the noble metal, that is formed by contact of the noble metal element or compound deposited on the surface of the catalyst with a sulfur compound. Non-limiting examples of sulfur compounds are $H_2S$, $C_nH_{2n+2}S$ where n=1-20, $C_nH_{2n+1}S_2$ where n=2-22 and $C_nH_{2n+1}S$ where n=2-22. The sulfur compound may be added before or during the aromatization reactions of the alkanes, i.e., the catalyst may be pretreated with the sulfur compound or the sulfur compound may be introduced with the hydrocarbon feed when it contacts the catalyst during the aromatization process. One method of pretreating the catalyst is that, prior to contact with the hydrocarbonaceous feed, the catalyst is treated first with hydrogen, second with a sulfur compound; and then again with hydrogen. The amount of sulfur on the catalyst is preferably in the range of from 10 ppm to 0.1 wt. %.

The chemical formula of the catalyst may be represented as:

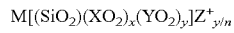

where M is a noble metal, such as platinum, X is a tetravalent element, Y is aluminum and, optionally, another trivalent element, Z is a cation with a valence of n, such as $H^+$, $Na^+$, $K^+$, $Rb^+$, $Cs^+$, $Ca^{2+}$, $Mg^{2+}$, $Sr^{2+}$ or $Ba^{2+}$, x varies from 0-0.15 and y is 0-0.125. According to the IUPAC recommendations, an example catalyst would be represented as:

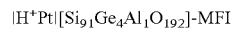

The zeolite catalyst of the present invention is applicable to a variety of conversion processes which use catalysts to convert a hydrocarbonaceous feed, i.e., a feed containing hydrocarbons, all or in part. These processes and the useful range of process conditions are all well known in the art. One example of use of the zeolite catalyst of the present invention is for aromatization of alkanes to aromatics. A zeolite catalyst of the present invention, such an MFI zeolite, may be used for the aromatization of alkanes having two to six carbon atoms per molecule to aromatics, such as benzene, toluene and xylenes. One particular example of a hydrocarbon conversion process is dehydrocyclodimerization of light hydrocarbons to aromatics, e.g., CYCLAR-type processing of $C_3$ alkane to aromatics, primarily benzene, toluene and xylenes. The CYCLAR (tradename) process is described in the paper "CYCLAR: One Step Processing of LPG to Aromatics and Hydrogen," by R. F. Anderson, J. A. Johnson and J. R. Mowry presented at the AIChE Spring National Meeting, Houston, Tex., Mar. 24-28, 1985. The dehydrocyclodimerization process increases carbon chain length by oligomerization, promotes cyclization, and dehydrogenates cyclics to their respective aromatics. The process operates at a temperature of about 350° C. to 650° C. and a relatively low pressure of about 10 to 2000 kPa gauge.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

2.65 g of germanium oxide and 3.28 g of sodium hydroxide were dissolved in 55.83 g deionized (DI) water to make solution 1. Solution 2 was made by dissolving 0.69 g sodium aluminate (57 wt % $Al_2O_3$, 35 wt % $Na_2O$ and 18 wt % $H_2O$) in 63.28 g DI water. Solution 1 and solution 2 were added to 57.23 g Ludox AS-40 sequentially. 40.25 g of 40 wt % tetrapropyl ammonium hydroxide was added to the above mixture. The mixture was stirred well using a Teflon coated magnetic stirrer. The pH of the mixture was adjusted with 9.24 g of glacial acetic acid so that the final gel pH was ~8.0. The $SiO_2/Al_2O_3$ ratio of the gel was calculated to be 98.78. The gel was loaded into a 300 mL stainless steel autoclave and heated at 160° C. for 36 hours. The contents were filtered and washed with DI water.

EXAMPLE 2

2.65 g of germanium oxide and 3.28 g of sodium hydroxide were dissolved in 55.83 g deionized (DI) water to make solution 1. Solution 2 was made by dissolving 0.97 g sodium aluminate (57 wt % $Al_2O_3$, 35 wt % $Na_2O$ and 18 wt % $H_2O$) in 63.28 g DI water. Solution 1 and solution 2 were added to 57.23 g Ludox AS-40 sequentially. 54.24 g of 40 wt % tetrapropyl ammonium hydroxide was added to the above mixture. The mixture was stirred well using a Teflon coated magnetic stirrer. The pH of the mixture was adjusted with 10.36 g of glacial acetic acid so that the final gel pH was ~9.5. The $SiO_2/Al_2O_3$ ratio of the gel was calculated to be 70.26. The gel was loaded into a 300 mL stainless steel autoclave and heated at 160° C. for 36 hours. The contents were filtered and washed with DI water.

COMPARATIVE EXAMPLE 7.97 g of germanium oxide and 14.62 g of sodium hydroxide were dissolved in 148.88 g deionized (DI) water to make solution 1. Solution 2 was made by dissolving 3.64 g sodium aluminate (57 wt % $Al_2O_3$, 35 wt % $Na_2O$ and 18 wt % $H_2O$) in 168.75 g DI water. Solution 1 and solution 2 were added to 152.61 g Ludox AS-40 sequentially. 185.97 g of 40 wt % tetrapropyl ammonium hydroxide was added to the above mixture. The mixture was stirred well using a Teflon coated magnetic stirrer. The pH of the mixture was adjusted with 41.51 g of glacial acetic acid so that the final gel pH was ~9.5. The $SiO_2/Al_2O_3$ ratio of the gel was calculated to be 50.00. The gel was loaded into a 1000 mL stainless steel autoclave and heated at 160° C. for 36 hours. The contents were filtered and washed with DI water.

The zeolites were bound with silica (50 wt % zeolite, 50 wt % silica) and sized to 20-40 mesh particles. The catalyst was then ion exchanged into the $H^+$ form and $Pt^{2+}$ was deposited on the catalyst by ion exchange. A final calcination at 300° C. was performed before the catalyst was tested.

The catalyst was pretreated with $H_2$ and $H_2S$. Any excess $H_2S$ was stripped with $H_2$ again. The catalyst was tested at 500° C. at 22 psig with 1 $h^{-1}$ WHSV propane. The results are shown in the figures.

Numerous modifications and variations of the present invention are possible in light of the above teachings. It is to be understood that, within the scope of the appended claims, the invention may be practiced other than as specifically described.

What is claimed as new and desired to be secured by Letter of Patent of the United States of America is:

1. A process for aromatization of alkanes to aromatics comprising contacting a hydrocarbonaceous feed of alkanes having two to six carbon atoms per molecule at aromatization conditions with a catalyst comprising:
   a) a zeolite having a mole ratio in the range of from about 70:1 to about 100:1 of an oxide of silicon ($SiO_2$) to an oxide of aluminum ($Al_2O_3$) and
   b) a noble metal deposited on the zeolite,
wherein the zeolite is synthesized by a process comprising:
   1) making a mixture by:
      (a) dissolving a germanium compound and sodium compound in water to make a first solution;
      (b) dissolving an aluminum compound in water to make a second solution;
      (c) adding the two solutions to colloidal silica sequentially;
      (d) adding a structuring agent;
   2) stirring the mixture;
   3) adjusting the pH of the mixture with acid to form a gel;
   4) heating the gel;
   5) filtering the gel; and
   6) washing filtered solids with water.

2. The process of claim 1 wherein the noble metal is present in the range of from 0.05% to 3% by weight.

3. The process of claim 1 wherein noble metal is present in the range of from 0.2% to 2% by weight.

4. The process of claim 1 wherein noble metal is present in the range of from 0.2% to 1.5% by weight.

5. The process of claim 2 wherein noble metal is platinum.

6. The process of claim 1 wherein the zeolite has a MFI, FAU, TON, MFL, VPI, MEL, AEL, AFI, MWW or MOR structure.

7. The process of claim 1 wherein the zeolite has a MFI structure.

8. The process of claim 1 wherein the zeolite additionally comprises tetravalent elements other than silicon and trivalent elements other than aluminum in the framework of the zeolite.

9. The process of claim 8 wherein the zeolite additionally comprises, tin, lead, zirconium, titanium, vanadium, chromium, gallium, boron, indium, thallium, iron, zinc or phosphorus.

10. The process of claim 1 wherein the hydrocarbonaceous feed additionally contains sulfur.

11. The process of claim 1 wherein the catalyst additionally contains sulfur.

12. The process of claim 1, wherein prior to contact with the hydrocarbonaceous feed, the catalyst is pretreated with a sulfur compound.

13. The process of claim 11 wherein the sulfur compound is $H_2S$, $C_nH_{2n+2}S$ where n=1-20, $C_nH_{2n+i}S_2$ where n=2-22 or $C_nH_{2n+i}S$ where n=2-22.

14. The process of claim 1 wherein the catalyst is represented by the formula $M[(SiO_2)(XO_2)_x(Y_2O_3)_y]Z^+_{y/n}$ where M is a noble metal, X is a tetravalent element, Y is aluminum and, optionally, another trivalent element, Z is a cation with a valence of n, x varies from 0-0.15 and y is 0-0.125.

15. The process of claim 14 wherein M is platinum.

16. The process of claim 14 wherein X is germanium and Y is aluminum.

17. The process of claim 14 wherein Z is $H^+$, $Na^+$, $K^+$, $Rb^+$, $Cs^+$, $Ca^{2+}$, $Mg^{2+}$, $Sr^{2+}$ or $Ba^{2+}$.

18. The process of claim 14 wherein Z is $H^+$.

19. The process of claim 1 wherein the catalyst is of the formula |$H^+Pt$|[$Si_{91}Ge_4Al_1O_{192}$]-MFI.

20. The process of claim 1 wherein the process is dehydrocyclodimerization of alkanes having two to six carbon atoms per molecule.

21. The process of claim 20 wherein the dehydrocyclodimerization process operates at a temperature of about 350° C. to 650° C. and a relatively low pressure of about 10 to 2000 kPa gauge.

22. The process of claim 1 wherein the catalyst is bound by oxides of magnesium, aluminum, titanium, zirconium, thorium, silicon, boron or mixtures thereof.

23. The process of claim 22 wherein the catalyst is bound by an oxide of silicon (silica).

24. A dehydrocyclodimerization process for aromatization of alkanes to aromatics comprising contacting a hydrocarbonaceous feed comprising propane at aromatization conditions with a catalyst pretreated with a sulfur compound comprising:
   a) a MFI zeolite additionally comprising germanium in the framework of the zeolite having a mole ratio in the range of from about 70:1 to about 100:1 of an oxide of silicon ($SiO_2$) to an oxide of aluminum ($Al_2O_3$) and
   b) platinum deposited on the zeolite,
wherein the zeolite is synthesized by a process comprising:
   1) making a mixture by:

(a) dissolving a germanium compound and sodium compound in water to make a first solution;
(b) dissolving an aluminum compound in water to make a second solution;
(c) adding the two solutions to colloidal silica sequentially;
(d) adding a structuring agent;
2) stirring the mixture;
3) adjusting the pH of the mixture with acid to form a gel;
4) heating the gel;
5) filtering the gel; and
6) washing filtered solids with water.

\* \* \* \* \*